US010702422B2

(12) United States Patent
Keiper

(10) Patent No.: US 10,702,422 B2
(45) Date of Patent: Jul. 7, 2020

(54) TAMPON RETAINER

(71) Applicant: Emily M Keiper, Fishers, IN (US)

(72) Inventor: Emily M Keiper, Fishers, IN (US)

(73) Assignee: VLAAR INNOVATIONS B.V., Midwoud (NL)

( * ) Notice: Subject to any disclaimer, the term of this patent is extended or adjusted under 35 U.S.C. 154(b) by 423 days.

(21) Appl. No.: 15/689,369

(22) Filed: Aug. 29, 2017

(65) Prior Publication Data
US 2018/0098888 A1 Apr. 12, 2018

Related U.S. Application Data

(60) Provisional application No. 62/405,458, filed on Oct. 7, 2016.

(51) Int. Cl.
| | |
|---|---|
| *A61F 13/34* | (2006.01) |
| *A61F 13/505* | (2006.01) |
| *A61F 13/84* | (2006.01) |
| *A61F 13/15* | (2006.01) |
| *A61F 13/00* | (2006.01) |

(52) U.S. Cl.
CPC .............. *A61F 13/34* (2013.01); *A61F 13/00* (2013.01); *A61F 13/15* (2013.01); *A61F 13/505* (2013.01); *A61F 2013/8476* (2013.01)

(58) Field of Classification Search
CPC ........ A61F 13/34; A61F 13/00; A61F 13/505; A61F 2013/8476; A61F 13/20; A61F 13/28; A61F 13/15; A61F 13/26; A61F 6/065; A61F 6/12; A61F 5/4553
See application file for complete search history.

(56) References Cited

U.S. PATENT DOCUMENTS

| | | | | |
|---|---|---|---|---|
| 3,481,335 A | * | 12/1969 | Beutlich | A61F 13/2051 604/11 |
| 3,521,637 A | * | 7/1970 | Waterbury | A61L 15/20 604/286 |
| 3,857,395 A | * | 12/1974 | Johnson | A61F 13/2051 604/14 |
| 2003/0125658 A1 | * | 7/2003 | Marvin | A61F 13/2051 604/13 |
| 2005/0080393 A1 | * | 4/2005 | Policappelli | A61F 13/2051 604/385.18 |
| 2010/0204666 A1 | * | 8/2010 | Feloney | A61F 5/4553 604/347 |
| 2011/0152742 A1 | * | 6/2011 | Winkel | A61F 13/266 604/15 |
| 2011/0295058 A1 | * | 12/2011 | Henriksson | A61F 2/005 600/37 |
| 2019/0151136 A1 | * | 5/2019 | Garriga | A61F 13/15 |

* cited by examiner

*Primary Examiner* — Tatyana Zalukaeva
*Assistant Examiner* — Gabriella E Burnette
(74) *Attorney, Agent, or Firm* — Adsero IP

(57) ABSTRACT

Novel tools and techniques are provided for implementing a tampon retainer to retain a string of a tampon in a vagina. In some embodiments, the tampon retainer comprises a body having a leading end and a trailing end. A fastener is located on the leading end of the body and is attachable to the tampon string. While the tampon and the tampon retainer are in use, the fastener maintains the entire tampon string within the vagina. The trailing end of the body of the tampon retainer is configured to extend from a vaginal opening when the tampon retainer is in use and a user can grasp the trailing end of the body to remove the tampon, the tampon string, and the tampon retainer from the vagina.

13 Claims, 2 Drawing Sheets

TAMPON RETAINER

RELATED APPLICATIONS

This application claims priority from U.S. Provisional Patent Application Ser. No. 62/405,458, filed Oct. 7, 2016, entitled "Tampon Retainer," which is hereby incorporated by reference.

TECHNICAL FIELD

The present disclosure is directed towards a tampon retainer and more particularly towards a device and method for retaining a tampon string within a vagina to prevent the tampon string from acting as a microbial vector for microbes outside the vagina and for facilitating removal of the tampon from the vagina.

BACKGROUND

Traditionally, after inserting a tampon into a vagina, a tampon string remains outside the vagina to remove the tampon after the tampon is used. However, by leaving the tampon string outside of the vagina, the tampon string can easily escape from a user's clothing (such as a person's underwear, swimsuit, leotard, skirt, or shorts) and be visible to others. When others see the tampon string, this can cause the user of the tampon to feel embarrassed, insecure, and anxious.

Further, by leaving the tampon string outside of the vagina, the tampon string can act as a microbial vector for microbes outside the vagina. Contaminates outside the vagina can travel up the tampon string or through the vaginal opening and remain stagnant in a woman's vagina or tampon. When the outside contaminates remain stagnant in a woman's vagina or tampon, bacteria flourish and toxicity levels in the vagina increase which can cause discomfort for the woman and/or bacterial infections in the vagina.

The present embodiments described herein are intended to overcome one or more of the problems discussed above.

SUMMARY

A first aspect is a tampon retainer. The tampon retainer comprises a body having a leading end and a trailing end. A fastener is located on the leading end of the body. The fastener is attachable to the tampon string. While the tampon and the tampon retainer are in use, the fastener maintains the entire tampon string within the vagina. The fastener can be a groove or a hook which attaches to the tampon string and, in use, secures the entire tampon string within the vagina. The trailing end of the body of the tampon retainer is configured to extend from a vaginal opening when the tampon retainer is in use and a user can grasp the trailing end of the body to remove the tampon, the tampon string, and the tampon retainer from the vagina.

The tampon retainer may come in a plurality of different sizes to accommodate a plurality of different user needs and user preferences. Further, the tampon retainer may be disposable to reduce bacterial infections that may occur due to repeated uses of the tampon retainer.

The body of the tampon retainer may be cylindrical to mimic the body of a tampon. Further, the cylindrical body of the tampon retainer may be no larger than the cylindrical body of a tampon.

Embodiments may include a flexible inner flange that extends radially from the leading end of the cylindrical body for insertion into the vagina. The fastener may be located on the leading surface of the flexible inner flange. Further, the flexible inner flange may be folded transverse on its axis for insertion into the vagina. After insertion into the vagina, the flexible inner flange may be configured to be sufficiently resilient to bias toward its unfolded state to secure the cylindrical body of the tampon retainer to a desired position on the vaginal wall.

The tampon retainer may also comprise a protrusion extending from the trailing end of the cylindrical body. A flexible outer flange may extend radially from the trailing end of the cylindrical body. A retractable tab, a retractable hook, or a retractable loop may be attached to the trailing end of the cylindrical body. These features (i.e., the protrusion, the flexible outer flange, the retractable tab, the retractable hook, and/or retractable loop) may extend from the vaginal opening and may be easily grasped by a user to remove the tampon retainer, tampon string, and tampon from the vagina.

The flexible outer flange may further be configured to extend out of the vaginal opening and be configured to cover the vaginal opening. The flexible outer flange may be sufficiently resilient to prevent foreign materials from entering the vaginal opening. The flexible outer flange may be configured to sit flat outside the vagina and/or include smooth rounded edges such that the flexible outer flange is not visible underneath a woman's clothes.

Another aspect is a method for using a tampon retainer. The method comprises providing a tampon retainer comprising a body having a leading and a trailing end, a fastener on the leading end of the body for maintaining the entire tampon string within a vagina while the tampon retainer is in use, and the trailing end being configured to, in use, extend from the vaginal opening for grasping by the user. The method further comprises attaching the tampon string to the fastener of the tampon retainer, inserting the entire tampon string and the leading end of the body within the vagina, and securing the tampon string and the leading end of the body in the vagina.

Another embodiment of the method further provides a flexible inner flange extending radially from the leading end of the body of the tampon retainer. The leading end of the body and the fastener may be secured in the vagina by folding the flexible inner flange transverse on its axis outside of the vagina, inserting the leading end of the body and the folded flexible inner flange into the vagina, and biasing the inner flange toward its unfolded state to secure the body of the tampon retainer to a desired position on the vaginal wall.

The method may further comprise providing a protrusion extending from the trailing end of the body. A flexible outer flange may also extend from the trailing end of the body. A retractable tab, a retractable hook, or a retractable loop may be attached to the trailing end of the body that extends from a vaginal opening. The body and the tampon string can then be removed from the vagina by pulling on at least one of these features (i.e., the protrusion, the flexible outer flange, the retractable tab, the retractable hook, and/or retractable loop) extending from the vaginal opening.

The flexible outer flange may further be configured to extend out of a vaginal opening, cover the vaginal opening, and be sufficiently resilient to prevent foreign materials from entering the vaginal opening may also be provided. The flexible outer flange may then be adjusted to a desired position on the vaginal opening so that the flexible outer flange completely covers the vaginal opening and prevents foreign materials from entering the vagina. The flexible outer flange may further be configured to sit flat outside the vagina and/or include smooth rounded edges such that the flexible outer flange is not visible underneath a woman's clothes.

By providing a tampon retainer with a fastener that secures the tampon string within the vagina, several advantages are realized. First, the tampon retainer can boost a woman's confidence when a she wears a swimsuit, leotard, skirt, or shorts. By securing the tampon string within the vagina with the tampon retainer and fastener, a user of the tampon retainer does not have to worry about the tampon string falling out of her clothing while she is walking, running, dancing, swimming, or participating in any other activity. Thus, a user does not have to worry that the tampon string is visible to others.

Second, by retaining the tampon string within the vagina with the tampon retainer, the tampon string is prevented from acting as a microbial vector for microbes and for other foreign material outside the vagina. Thus, the tampon retainer helps women to confidently wear a tampon for longer periods of time without the risk of the tampon string acting as a microbial vector for microbes and foreign material to enter the vagina.

DETAILED DESCRIPTION

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Figure 1:
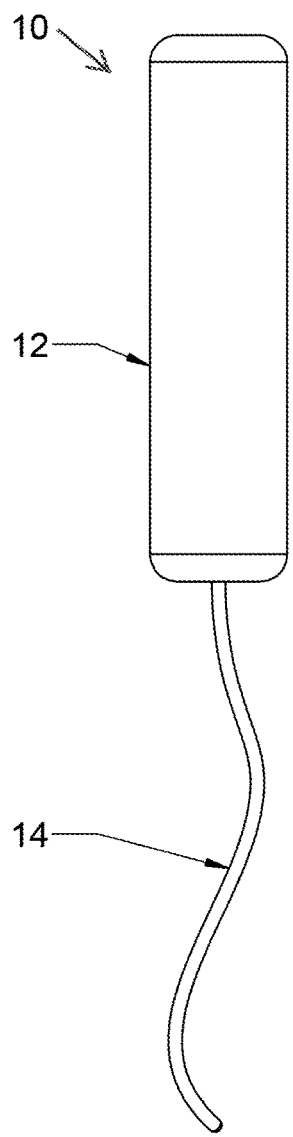
FIG. 1 is a plan view of a tampon.

FIG. 1 is a plan view of a tampon 10. The tampon 10 has a tampon body 12 and a tampon string 14.

Figure 2:
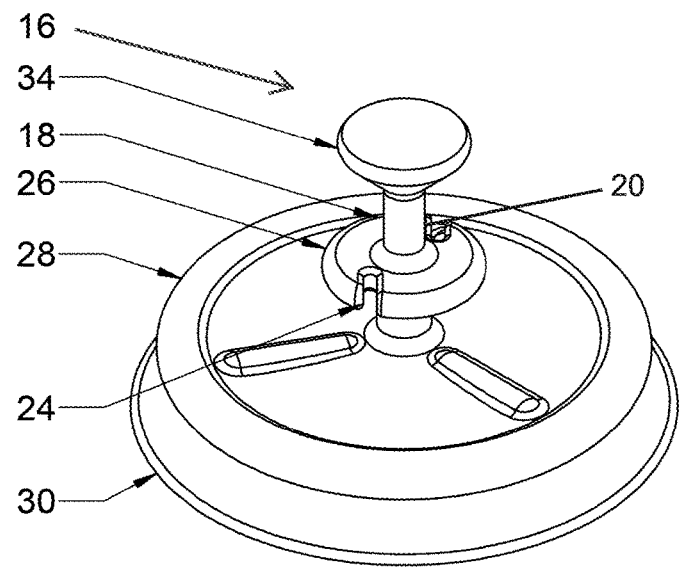
FIG. 2 is a perspective view of an embodiment of a fully assembled tampon retainer in accordance with the present disclosure.

A perspective view of an embodiment of a fully assembled tampon retainer 16 is illustrated in FIG. 2. The tampon retainer 16 may come in a plurality of different sizes to accommodate a plurality of different needs and user preferences. Further, the tampon retainer 16 may be disposable to reduce bacterial infections that may occur due to repeated uses of the tampon retainer 16. The tampon retainer 16 may also be washable and reusable to reduce the cost of purchasing new tampon retainers.

Figure 3:
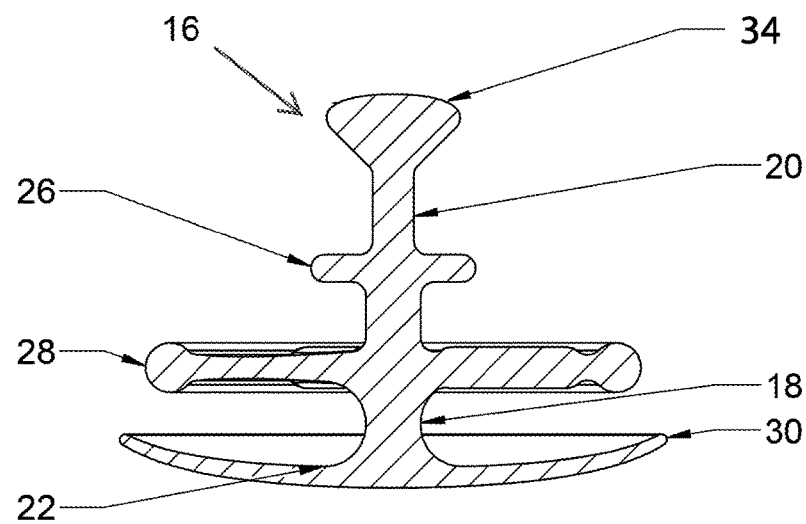
FIG. 3 is a sectional view of the tampon retainer of FIG. 2.
Figure 4:
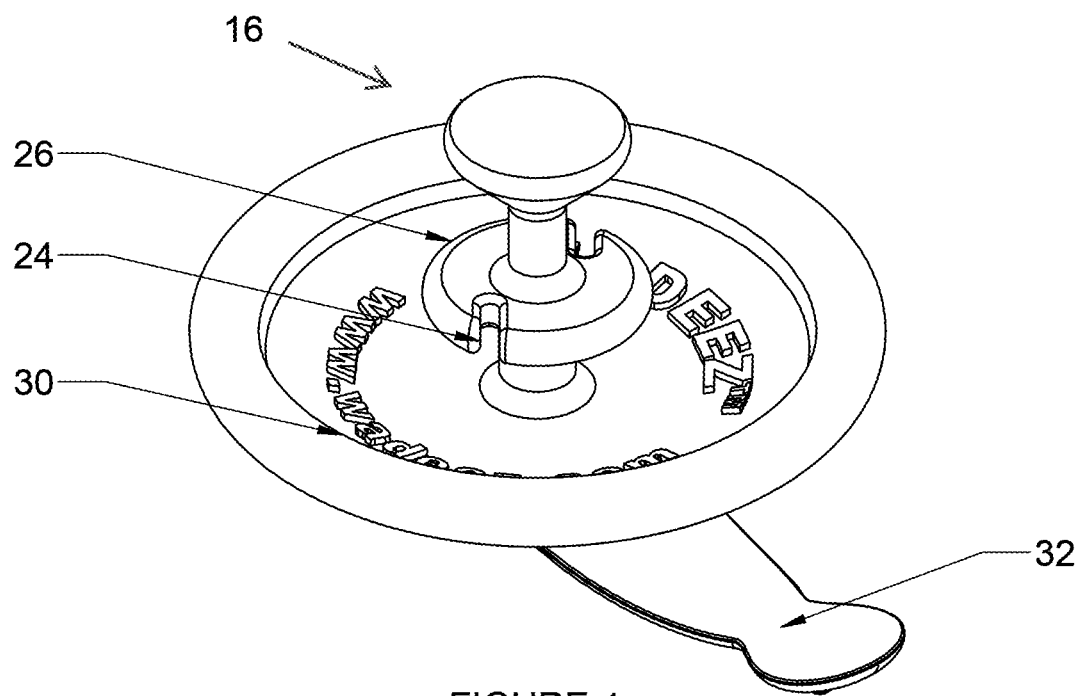
FIG. 4 is a perspective view of a second embodiment of a fully assembled tampon retainer in accordance with the present disclosure.
Figure 5:
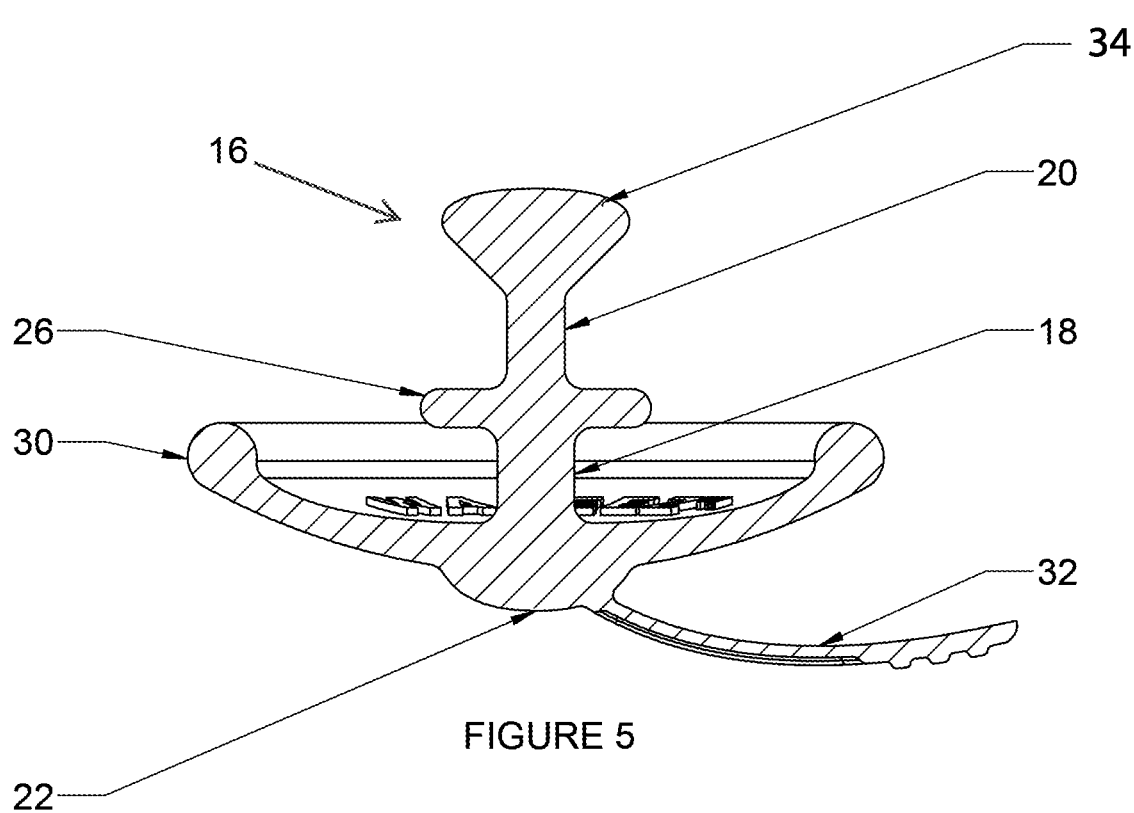
FIG. 5 is a sectional view of the tampon retainer of FIG. 4.

The tampon retainer 16 (shown in FIGS. 2-5) comprises a body 18 with a leading end 20 and a trailing end 22 (shown in FIGS. 3 and 5). The leading end 20 of the body 18 is inserted into the vagina while the tampon retainer 16 is in use. The leading end 20 of the body 18 may be grasped by the vaginal muscle to secure the tampon retainer 16 in the vagina. The trailing end 22 (shown in FIGS. 3 and 5) of the body 18 is configured to extend from the vaginal opening of the user so that the user may grasp the trailing end 22 of the body 18 to remove the leading end 20 of the body 18 from the vagina. The trailing end 22 of the body 18 may be formed and/or coated in a substance that allows for easy grasping by a user. The trailing end 22 of the body 18 may also lie flat or be sufficiently smooth and rounded such that it is not visible to others on the outside of a woman's clothing.

The body 18 of the tampon retainer 16 may be cylindrical to mimic a cylindrical tampon body 12 of a tampon 10. Further, the body 18 may have a diameter no larger than a cylindrical tampon body 12 of the tampon 10. By mimicking the cylindrical tampon body 12 of the tampon 10 and ensuring that the diameter of the cylindrical body 18 of the tampon retainer is no larger than the diameter of the cylindrical body 12 of the tampon 10, the tampon retainer 16 is as comfortable as a tampon and as easy to insert and use as a tampon.

An end protrusion 34 may further be provided (although it is not required) on the leading end 20 of the body 18. The end protrusion 34 may interact with the vaginal opening to provide easy insertion of the tampon retainer 16 into the vagina. In some embodiments, the circumference of the end protrusion 34 may be larger than the circumference of the body 18 to aid in inserting the tampon retainer 16 into the vagina.

A fastener 24 may be located on the body 18. The fastener 24 is attachable to the tampon string 14. In use, a user may wrap at least a portion of the tampon string 14 around the body 18 before securing an end of the tampon string 14 in the fastener 24. By having the circumference of the end protrusion 34 be larger than the circumference of the body 18, the string 14 of the tampon 10 may be protected and the likelihood that the tampon string 14 will contact the vaginal wall and dislodge from the fastener 24 while the tampon retainer 16 is being inserted/removed will be reduced.

The fastener 24 may comprise at least one groove that is attachable to the tampon string 14. By providing more than one groove, a tampon string 14 may be secured in at least two places to ensure that the tampon string 14 is removed with the tampon retainer 16 from the vagina. Embodiments may include the body 18 and/or the fastener 24 being made of a resilient material so that a tampon string 14 is wedged into the groove and held in place by the resilient nature of the body and/or fastener material. The fastener 24 may also be a hook or any other feature that is attachable to the tampon string 14.

The fastener 24 may be at least one of located directly on the leading end 20 of the body 18, located on the end protrusion 34, or located on a cylindrical protrusion 26 extending from the body 18. The cylindrical protrusion 26 may be smaller than end protrusion 34. By having a smaller cylindrical protrusion 26 than end protrusion 34, the risk that the tampon string 14 will become stuck in the vagina is reduced because it is less likely that the tampon string 14 will contact the vaginal wall while the tampon retainer is being removed and/or inserted.

In use, the fastener 24 maintains the entire tampon string 14 within the vagina. By securing the entire tampon string 14 within the vagina, a user of the tampon 10 does not have to worry about the tampon string 14 falling out of her clothing while she is walking, running, dancing, swimming, or participating in any other activity. Further, by securing the entire tampon string 14 within the vagina, a user of the tampon 10 does not have to worry that the tampon string 14 will act as a microbial vector for microbes and other foreign material outside the vagina.

A flexible inner flange 28 (shown in FIGS. 2 and 3) may extend radially from the cylindrical body 18. In use, the flexible inner flange 28 is inserted into the vagina and the purpose of the flexible inner flange 28 is to secure the tampon retainer 16 to a desired position on a vaginal wall. The flexible inner flange 28 may be configured to be folded transverse on its axis and may be configured to be sufficiently resilient to bias, after insertion into the vagina, toward its unfolded state to secure the cylindrical body 18 to a desired position on the vaginal wall. By providing a flexible inner flange 28 that is slightly larger than the cylindrical body 18, it is easier for the vaginal muscles to grasp and for the vaginal muscles to maintain the tampon retainer 16 in a comfortable position in the vagina. Further, the flexible inner flange 28 ensures that the tampon retainer 16 does not move and cause discomfort while the tampon retainer 16 is in use.

Further, as shown in FIGS. 2 and 3, the fastener 24 can be located on a cylindrical protrusion 26 of the cylindrical body 18. The circumference of cylindrical protrusion 26 may be smaller than the circumference of the flexible inner flange 28. By providing a smaller cylindrical protrusion 26, the risk that the tampon string 14 will become stuck in the vagina is reduced because it is less likely that the tampon string 14 will contact the vaginal wall while the tampon retainer 16 is being inserted and/or removed from the vagina. The flexible inner flange 28 may further be capable of folding around the fastener 24 and the tampon string 14 on the cylindrical protrusion 26 as the tampon retainer 16 is removed from the vagina. This functionality also reduces the likelihood that the tampon string 14 will contact the vaginal wall and dislodge from the fastener 24 while the tampon retainer is being removed.

As shown in FIGS. 2, 3, 4, and 5, a flexible outer flange 30 can extend radially from the trailing end 22 of the cylindrical body 18. The flexible outer flange 30 may be configured to extend out of a vaginal opening, configured to cover the vaginal opening, and configured to be sufficiently resilient to prevent foreign materials from entering the vaginal opening. The flexible outer flange 30 can sit flat outside the vagina and/or include smooth rounded edges such that the flexible outer flange 30 is not visible underneath a woman's clothes.

The flexible outer flange 30 can also be inserted just inside the vagina by folding the flexible outer flange 30 transverse on its axis. After insertion into the vagina, the flexible outer flange 30 may be configured to be sufficiently resilient to bias toward its unfolded state to further secure the cylindrical body 18 of the tampon retainer 16 to a desired position on the vaginal wall. By inserting the flexible outer flange 30 just inside the vagina, the flexible outer flange 30 can act to seal with the vaginal opening and prevent/inhibit foreign material from entering the vaginal opening. By sealing the vaginal opening with the flexible outer flange 30, it is much harder for foreign contaminates and bacteria to enter the vaginal opening and cause can discomfort for the woman and/or bacterial infections in the vagina. Further, inserting the flexible outer flange 30 into the vagina ensures that the tampon retainer 16 does not move and is securely held within the vagina.

Further, as shown in FIGS. 4 and 5, the fastener 24 can be located on a cylindrical protrusion 26 of the cylindrical body 18. The circumference of cylindrical protrusion 26 may be smaller than the circumference of the flexible outer flange 30. The flexible outer flange 30 (when inserted just inside the vaginal opening) may further be capable of folding around the fastener 24 and the tampon string 14 on the cylindrical protrusion 26 as the tampon retainer 16 is removed from the vagina. This functionality reduces the likelihood that the tampon string 14 will contact the vaginal wall and dislodge from the fastener 24 while the tampon retainer 16 is being removed from the vagina.

As shown in FIGS. 4 and 5, a protrusion 32 may extend from the trailing end of the body 22 and from the vaginal opening when the tampon retainer is in use. The protrusion 32 extends from the trailing end 22 of the cylindrical body 18 to remove the leading end 20 of the cylindrical body 18 from the vagina. The protrusion 32 may be provided directly on the trailing end 22 of the cylindrical body 18 or it may extend from a leading end of the flexible outer flange 30. The protrusion 32 may be formed and/or coated in a substance that allows for easy grasping by a user. The protrusion 32 may also sit flat and/or be sufficiently smooth and rounded such that it is not visible to others on the outside of a woman's clothing. The protrusion 32 could also be at least one of a flexible outer flange extending radially from the trailing end of the cylindrical body, a retractable tab, a retractable hook, or a retractable loop.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A tampon retainer comprising:
   a body having a leading and trailing end;
   a cylindrical protrusion extending radially from the body between the leading end and the trailing end;
   a fastener on the cylindrical protrusion attachable to a tampon string for, in use, maintaining the entire tampon string within a vagina;
   the trailing end of the body being configured to, in use, extend from a vaginal opening for grasping by a user.

2. The tampon retainer of claim 1, wherein the tampon retainer comes in a plurality of different sizes to accommodate a plurality of different needs.

3. The tampon retainer of claim 1, wherein the fastener is at least one groove which attaches to the tampon string.

4. The tampon retainer of claim 1, wherein the body is cylindrical.

5. The tampon retainer of claim 4, wherein the diameter of the cylindrical body is no larger than the diameter of a cylindrical body of a tampon.

6. The tampon retainer of claim 4, further comprising:
   a flexible inner flange, for insertion into the vagina, extending radially from the cylindrical body between the cylindrical protrusion and the trailing end.

7. The tampon retainer of claim 6, wherein the flexible inner flange is configured to be folded transverse on its axis and configured to be sufficiently resilient to bias, after insertion into the vagina, toward its unfolded state to secure the cylindrical body to a desired position on a vaginal wall.

8. The tampon retainer of claim 4, further comprising:
at least one of a protrusion extending from the trailing end of the cylindrical body, wherein the protrusion further comprises a retractable tab attached to the trailing end of the cylindrical body and extending from a vaginal opening to remove the body from the vagina; and
a flexible outer flange extending radially from the trailing end of the cylindrical body.

9. The tampon retainer of claim 4, further comprising:
a flexible outer flange extending radially from the trailing end of the cylindrical body, wherein the flexible outer flange is configured to extend out of a vaginal opening, configured to cover the vaginal opening, and configured to be sufficiently resilient to prevent foreign materials from entering the vaginal opening.

10. A method for using a tampon retainer comprising:
providing a tampon retainer comprising a body having a leading and a trailing end, a fastener on the leading end of the body attachable to a tampon string for, in use, maintaining the entire tampon string within a vagina, and the trailing end of the body being configured to, in use, extend from the vaginal opening for grasping by a user;
attaching the tampon string to the fastener of the tampon retainer;
inserting the entire tampon string and the leading end of the body within the vagina; and
securing the tampon string and leading end of the body in the vagina.

11. The method of claim 10 further comprising:
providing a flexible inner flange extending radially from the leading end of the body;
securing the leading end of the body and the fastener in the vagina by folding the flexible inner flange transverse on its axis outside of the vagina;
inserting the leading end of the body and the folded flexible inner flange into the vagina; and
biasing the inner flange toward its unfolded state to secure the body to a desired position on a vaginal wall.

12. The method of claim 10 further comprising:
providing at least one of a protrusion extending from the trailing end of the body, wherein the protrusion comprises a retractable tab attached to the trailing end of the body and extending from a vaginal opening;
providing a flexible outer flange extending from the trailing end of the body; and
removing the body and the tampon string attached to the fastener from the vagina by pulling on at least one of the protrusion extending from the trailing end of the body or the flexible outer flange extending from the trailing end of the body.

13. The method of claim 10 further comprising:
providing a flexible outer flange extending radially from the trailing end of the body, wherein the flexible outer flange is configured to extend out of a vaginal opening, configured to cover the vaginal opening, and configured to be sufficiently resilient to prevent foreign materials from entering the vaginal opening; and
adjusting the flexible outer flange so the flexible outer flange completely covers the vaginal opening.

* * * * *